United States Patent
Spivack

(10) Patent No.: US 6,486,364 B2
(45) Date of Patent: Nov. 26, 2002

(54) AMINE MODIFIED CATALYSTS FOR BISPHENOL PRODUCTION

(75) Inventor: James Lawrence Spivack, Cobleskill, NY (US)

(73) Assignee: General Electric Company, Niskayuna, NY (US)

( * ) Notice: Subject to any disclaimer, the term of this patent is extended or adjusted under 35 U.S.C. 154(b) by 5 days.

(21) Appl. No.: 09/741,628

(22) Filed: Dec. 19, 2000

(65) Prior Publication Data

US 2002/0123656 A1 Sep. 5, 2002

(51) Int. Cl.[7] .................................................. C07C 39/16
(52) U.S. Cl. ...................... 568/728; 502/159; 568/727
(58) Field of Search .................................. 568/727, 728; 502/159

(56) References Cited

U.S. PATENT DOCUMENTS

| 3,394,089 A | * | 7/1968 | McNutt |
| 4,396,728 A | * | 8/1983 | Faler |
| 4,423,252 A | * | 12/1983 | Maki |
| 5,475,154 A | * | 12/1995 | Lundquist |

FOREIGN PATENT DOCUMENTS

| EP | 771589 A1 | | 5/1997 |
| JP | 8-325185 | * | 12/1996 |
| JP | 10-314595 | * | 12/1998 |

* cited by examiner

*Primary Examiner*—Michael L. Shippen
(74) *Attorney, Agent, or Firm*—Andrew J. Caruso; Noreen C. Johnson

(57) ABSTRACT

The acid catalyzed condensation of phenol with acetone in the presence of a thiol promoter to produce bisphenol A is found to occur with greater overall selectivity when the catalyst employed is an amine modified acidic resin catalyst. Amine modified acidic resin catalysts are prepared from acidic resins such as sulfonated polystyrene by neutralization of a portion of the acidic functional groups present with an amine such as pyridine. Where the thiol promoter is itself an amine the use of an amine such as pyridine as the modifying agent reduces the amount of thiol promoter required to achieve high selectivity.

27 Claims, No Drawings

AMINE MODIFIED CATALYSTS FOR BISPHENOL PRODUCTION

BACKGROUND OF THE INVENTION

This invention relates to amine modified acidic resin catalysts and their use in the reaction of hydroxyaromatic compounds with aldehydes and ketones in the presence of a thiol promoter to afford bisphenols, such as bisphenol A (BPA).

Bisphenols, as exemplified by BPA, are widely employed in the manufacture of polymeric materials and are typically prepared by condensation of a hydroxyaromatic compound with an aldehyde or ketone in the presence of an acidic catalyst. Bisphenol A is the principal monomer used in the manufacture of bisphenol A polycarbonate, a commercial engineering thermoplastic material. The manufacture of bisphenol A from acetone and phenol is practiced globally on a large scale with hundreds of millions of pounds of BPA produced annually. Typically, phenol is reacted with acetone in the presence of an acidic catalyst and a thiol promoter. The thiol promoter acts to improve the rate and selectivity of BPA formation in the acid catalyzed condensation of phenol with acetone. Many different combinations of acidic catalysts and thiol promoters have been investigated and some thiol promoters such as 3-mercaptopropionic acid have been employed in the commercial scale production of BPA. Notwithstanding earlier research efforts and their attendant impressive process improvements in the manufacture of bisphenols, such as bisphenol A, there is a continuing need to improve further both the rate and selectivity of bisphenol formation in the acid catalyzed condensation of hydroxyaromatic compounds with aldehydes or ketones.

BRIEF SUMMARY OF THE INVENTION

In one aspect the present invention relates to a method for making a bisphenol, said method comprising contacting a mixture comprising a hydroxyaromatic compound and a ketone or an aldehyde with an amine modified acidic resin catalyst at a temperature in a range between about 25° C. and about 95° C. in the presence of a thiol promoter. In a further aspect, the present invention relates to amine modified acidic resin catalysts.

DETAILED DESCRIPTION OF THE INVENTION

The present invention may be understood more readily by reference to the following detailed description of preferred embodiments of the invention and the examples included herein. In this specification and in the claims which follow, reference will be made to a number of terms which shall be defined to have the following meanings.

The term "amine modified acidic resin catalyst" as used herein refers to an acidic resin, a portion of the acidic functional groups of which have been neutralized by treatment with an amine. For example a sulfonated polystyrene resin in which about 5 to 50 percent of the SO3H groups have been converted to the corresponding pyridium salts upon treatment of the resin with the corresponding amount of the amine, pyridine, constitutes an amine modified acidic resin catalyst. The amine employed is distinct from any thiol promoter which itself comprises an amine group. Where the thiol promoter contains an amine group, for example as in cysteamine, the amine modified acidic resin catalyst is understood to comprise at least one other amine which is not a thiol promoter.

"BPA" is herein defined as bisphenol A and is also known as 2,2-bis(4-hydroxyphenyl)propane, 4,4'-isopropylidenediphenol and p,p-BPA.

"o,p-BPA" is herein defined as o,p-bisphenol A and is also known as 2-(2-hydroxyphenyl)-2-(4-hydroxyphenyl)propane and 2,4'-isopropylidenediphenol.

As used herein the term "aromatic radical" refers to a radical having a valency of at least one and comprising at least one aromatic group. Examples of aromatic radicals include phenyl, pyridyl, furanyl, thienyl, imidazolyl, naphthyl, phenylene and biphenyl groups. The term includes groups containing both aromatic and aliphatic components, for example a benzyl group. Further, a $C_3$–$C_{40}$ aromatic radical is an aromatic radical comprising between 3 and 40 carbon atoms. The 2-imidazolyl group (i) illustrates a $C_3$ aromatic radical.

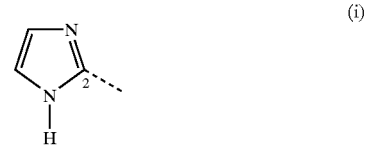

(i)

As used herein the term "aliphatic radical" refers to a radical having a valency of at least one and comprising a linear or branched array of atoms which is not cyclic. The array may include heteroatoms such as nitrogen, sulfur and oxygen or may be composed exclusively of carbon and hydrogen. Examples of aliphatic radicals include methyl, methylene, ethyl, ethylene, hexyl, and hexamethylene groups.

As used herein the term "cycloaliphatic radical" refers to a radical having a valency of at least one and comprising an array of atoms which is cyclic but which is not aromatic. The array may include heteroatoms such as nitrogen, sulfur and oxygen or may be composed exclusively of carbon and hydrogen. Examples of cycloaliphatic radicals include cyclopropyl, cyclopentyl cyclohexyl and tetrahydrofuranyl groups.

As used herein the term "carbamyl group" refers to a functional group comprising the array of atoms OCONH. For example a carbamyl group is present the product of reaction of an alcohol with an isocyante as illustrated by the compound 1-naphthyl methylcarbamate, CAS No. 63-25-2.

As used herein the term "Boc group" refers to a an amine protecting group comprising the tertiary-butoxycarbonyl moiety. The combination of a nitrogen atom bearing both a hydrogen atom and the Boc group is an example of a carbamyl group.

The term "thiol promoter" as used herein refers to a molecule incorporating a thiol (SH) group. The thiol promoter acts to improve the rate and selectivity of bisphenol formation when a hydroxyaromatic compound is condensed with an aldehyde or ketone in the presence of an acidic catalyst relative to the same reaction carried out in the absence of the thiol promoter.

The term "silylmethanethiol" refers to a thiol compound in which a silicone atom and sulfur atom are each attached to the same carbon atom.

The instant invention provides a method of preparing a bisphenol, such as bisphenol A, by acid catalyzed condensation of a hydroxyaromatic compound, such as phenol, with an aldehyde, such as butanal, or a ketone, such as acetone, in the presence of a thiol promoter and an amine modified acidic resin catalyst.

The instant invention further provides amine modified acidic resin catalysts, which when used in the preparation of bisphenols, such as bisphenol A, provide selectivity advantages over known acidic resin catalyst systems. Amine modified acidic resin catalysts are prepared upon treatment of a polymeric material comprising acidic functional groups, such as sulfonic acid groups, with an amine in an amount such that between about 0.1 and about 50 percent of the acidic functional groups are neutralized. The amine modified acidic resins of the present invention are more selective catalysts, as measured by the greater selectivity for p,p-BPA formation observed when phenol and acetone are reacted in the presence of said amine modified acidic resin and a thiol promoter, relative to known acidic resin catalysts such as sulfonated polystyrene in combination with a thiol promoter.

Typically, the acidic resin catalyst which is converted to an amine modified acidic resin catalyst is a sulfonated polystyrene derivative comprising structural units I. Polymeric acidic resins comprising structure I are exemplified by

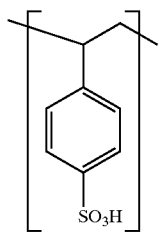

I

Amberlyst® 131, Amberlyst® 15 and Amberlyst® 36, all of which are strongly acidic ion exchange resins available from the Rohm and Haas Company.

Other suitable polymeric acidic resin catalysts which may be converted into the amine modified acidic resin catalysts of the present invention include Nafion® perfluorinated acidic resins available from the Dupont Company.

Typically, the acidic resin catalyst possesses between about 0.1 and about 6, preferably between about 2 and about 5 milliequivalents of acidic functional group per gram of resin. Typically, the acidic functional group is a sulfonic acid group. In the practice of the present invention it has been found advantageous to treat the acidic resin catalyst with a sufficient amount of an amine to neutralize between about 0.1 and about 50 percent, preferably between about 5 and about 40 percent and most preferably between about 20 and about 35 percent of the acidic functional groups present in the acidic resin. Thus, treatment of one gram of a sulfonated polystyrene resin comprising structural units I possessing about 5 milliequivalents per gram resin of sulfonic acid groups ($SO_3H$ groups) with 1 milliequivalent of an amine, such as pyridine, affords an amine modified acidic resin catalyst in which 20 percent of the sulfonic acid groups have been converted to the corresponding pyridinium sulfonate salt, assuming complete reaction between the pyridine and the sulfonic acid groups of the resin. The amine modified acidic resin catalysts of the present invention are shown to be superior in terms of product selectivity relative to unmodified acidic resin catalysts. Product selectivity may be expressed as the weight percent of the p,p-bisphenol isomer in the product mixture relative to the weight percent o,p-bisphenol isomer. Additionally, product selectivity may be expressed as the weight percent of the desired p,p-bisphenol product relative to all other products formed.

Amines suitable for the preparation of amine modified acidic resin catalysts include aliphatic, cycloaliphatic and aromatic amines which are sufficiently basic to permit attachment of the amine to the resin, said attachment being based upon an ionic bond between the acidic group and the amine, such as is found in a pyridinium sulfonate.

Aliphatic amines are exemplified by triethylamine, trimethylamine, tributylamine and N,N-dimethylbutyamine. Cycloaliphatic amines are exemplified by piperidine, morpholine, 1,8-diazabicyclo[5.4.0]undec-7ene (DBU) and diazabicylco[2.2.2]octane (Dabco). Aromatic amines are illustrated by pyridine, imidazole, quinoline and piperazine. Generally, simple $C_1$–$C_{10}$ aliphatic, $C_4$–$C_{10}$ cycloaliphatic and $C_5$–$C_9$ aromatic amines are preferred.

Thiol promoters which may be employed include aliphatic, cylcoaliphatic and aromatic thiols which may be substituted by a basic group such as an amine or an acidic group such as a carboxylic acid. The thiol promoter may be used as a "bulk" promoter, that is a thiol promoter which is not adapted for attachment to the amine modified acidic resin, or an "attached" promoter. Where the thiol promoter contains a basic functional group such as an amine said thiol promoter may be attached to amine modified acidic resin catalyst and is referred to as an "attached" promoter. Functional groups present in the thiol promoter, other than amino groups, which facilitate the attachment of the thiol promoter to the amine modified acidic resin catalyst include amido, imido and carbamyl groups as are found in amides, imides and carbamates, respectively.

Bulk thiol promoters include cylcoaliphatic thiols such as cyclohexanethiol and cyclopentanethiol, aromatic thiols such as thiophenol and benzylthiol, and aliphatic thiols such as butanethiol, hexanethiol, octadecanethiol and 3-mercaptopropionic acid.

Attached thiol promoters include 2-mercaptomethylpyridine, cysteamine, and 4-aminobutanethiol immobilized in an amine modified acidic resin catalyst, for example a sulfonated polystyrene in which about 20 percent of the sulfonic acid groups have been neutralized with pyridine.

Among the aliphatic thiols suitable for use in the present invention silylmethanethiols having structure II have been found to be particularly effective thiol promoters.

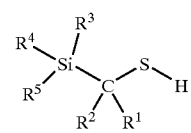

II wherein $R^1$ and $R^2$ are each independently hydrogen, a $C_1$–$C_{40}$ aliphatic radical, a $C_3$–$C_{40}$ aromatic radical, a $C_3$–$C_{40}$ cycloaliphatic radical, or $R^1$ and $R^2$ together form a $C_3$–$C_{40}$ cycloaliphatic radical or a $C_4$–$C_{40}$ aromatic radical;

$R^3$–$R^5$ are each independently a $C_1$–$C_{40}$ aliphatic radical, a $C_3$–$C_{40}$ aromatic radical, or a $C_3$–$C_{40}$ cycloaliphatic radical; or any two of the groups $R^3$–$R^5$ together form a $C_5$–$C_{40}$ cycloaliphatic radical or $C_5$–$C_{40}$ aromatic radical; or the groups $R^3$–$R^5$ together form a $C_9$–$C_{40}$ cycloaliphatic radical or $C_{10}$–$C_{40}$ aromatic radical.

Where any of the groups R1–R5 of structure II contains a basic functional group, such as an amino group, the silylmethanethiol promoter may be attached to the amine modified acidic resin catalyst. Functional groups present in the silylmethanethiol, other than amino groups, which facilitate the attachment of the promoter to the amine modified acidic resin catalyst include amido, imido and carbamyl groups as are found in amides, imides and carbamates, respectively.

Silylmethanethiols having structure II are known in the chemical

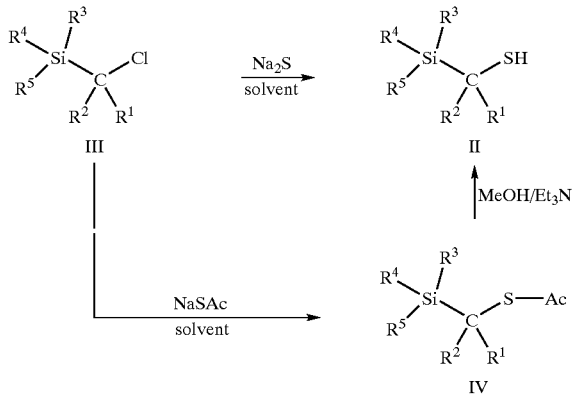

literature and methods for their preparation have been described in, for example, J. Org. Chem. 53(5) 844 (1987); J. Org. Chem. 51(18) 3428 (1986); and Tetrahedron Letters 26 (11) 1425 (1985). In some instances silylmethanethiols having structure II are commercially available as in the case of trimethylsilylmethanethiol which is available from TCI Chemical Company, Portland, Oreg. Other members of this class may be prepared by reaction of a chloromethylsilane having structure III with a sulfur nucleophile such as sodium sulfide, sodium thioacetate or thiourea. Where sodium sulfide is employed the silylmethanthiol II is obtained directly. Where the thioacetate is employed as a nucleophile, acetate derivative IV is obtained. The acetate derivative IV is readily converted to the corresponding thiol II upon solvolysis, for example upon heating acetate derivative IV with methanol in the presence of a basic catalyst such as triethylamine.

Chloromethylsilicon compounds corresponding to structure III may be prepared by a variety of methods, among them the hydrosilylation reaction of olefins having structure V with a chloromethylsilane VI incorporating a silicone hydride function. Thus, olefin V in which radical $R^6$ corresponds to a two carbon lower homolog of radical $R^5$ may be reacted with chloromethylsilane VI in the presence of a noble metal catalyst to afford chloromethylsilicon derivative III.

A variety of reaction conditions may be employed for the conversion

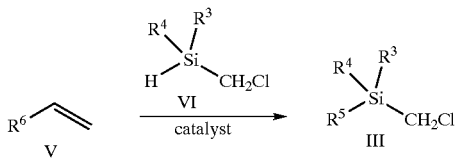

of chloromethylsilanes III into silylmethanethiols II and silylmethanethiol acetate derivatives IV. Typically, the chloromethylsilane III is combined in a polar solvent such as methanol or dimethylformamide with a slight excess of sodium sulfide or sodium thioacetate and the mixture us stirred at a temperature between about 0° C. and about 100° C. until the starting chloromethylsilane III has been consumed as judged by gas chromatography, thin layer chromatography or like analytical technique. Thereupon, the reaction mixture may be distributed between water and a solvent such as methylene chloride, toluene or ethyl acetate. The organic layer is then washed with water to complete the removal of inorganic salts and then dried over a suitable drying agent such as magnesium sulfate. Filtration and solvent evaporation affords the crude product which may be employed as a thiol promoter for BPA production in its crude state, or purified, for example by column chromatography or recrystallization, prior to such use.

Examples of silylmethanethiols which may be used as promoters for bisphenol production include, but are not limited to, trimethylsilylmethanethiol, triethylsilylmethanethiol, tripropylsilylmethanethiol, tributylsilylmethanethiol, 1-trimethylsilyl-1-ethylmethanethiol and 1-trimethylsilyl-1-benzylmethanethiol.

Where the silylmethanethiol promoter is to be used as a bulk promoter, the preferred silylmethanethiol promoter is trimethylsilylmethanethiol owing to its availability, ease of preparation and recovery or removal from the reaction product.

In some instances it may be advantageous to employ a silylmethanethiol derivative such as trimethylsilylmethanethiol acetate in the process of the present invention. Under such circumstances it is believed that the silylmethanethiol acetate is converted to the active silylmethanethiol promoter under the reaction conditions. Silylmethanethiol acetates and other silylmethanethiol derivatives which afford a silylmethanethiol under the reaction conditions are advantageously employed at about the same levels as the silylmethanethiol itself.

In some instances the silylmethanethiol promoter may function as an attached promoter, as is the case of those silylmethanethiols which incorporate an amine function which may be used to form an attachment to amine modified acidic resin catalyst. The attachment of the silylmethanethiol to the amine modified acidic resin catalyst may be based upon a strong hydrogen bonding interaction or a covalent bond. Examples of silylmethanethiols which may be used as attached promoters for bisphenol production include 3-aminopropyldimethylsilylmethanethiol, 3-N-methylaminopropyldimethylsilylmethanethiol, 3-N,N-dimethylaminopropyldimethylsilylmethanethiol, 3-(1-piperadinyl)propyldimethylsilylmethanethiol and 2-(4-pyridyl)ethyldimethylsilylmethanethiol.

In addition to silylmethanethiols which incorporate a free amino function, derivatives of such materials incorporating acylated thiol groups and protected amine groups may also be employed. Thus, the N-Boc-3-aminopropyldimethylsilylmethanethiol acetate derivative VII is found to function as an effective attached promoter for bisphenol production. Thioacetate VII is believed to be converted to 3-aminopropyldimethyl-silylmethanethiol VIII under the conditions used to prepare bisphenols.

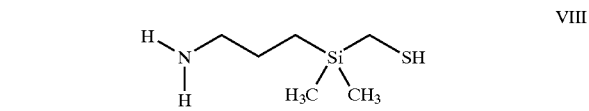

As noted, the instant invention provides a method of preparing a bisphenol, such as bisphenol A, wherein an amine modified acidic resin catalyst is employed together with a thiol promoter to effect the condensation of a hydroxyaromatic compound with an aldehyde or a ketone. Examples of hydroxyaromatic compounds include phenol, o-cresol, m-cresol, 2-t-butylphenol, 2-propylphenol and 1-naphthol. Examples of aldehydes include formaldehyde, acetaldehyde, propionaldehyde and butanal. Examples of ketones include acetone, cyclohexanone; 3,3,5-trimethylcyclohexanone, 2-butanone and fluorenone.

A wide variety of bisphenols; such as 2,2-bis(4-hydroxyphenyl)propane; 2,2-bis(4-hydroxy-3-methylphenyl)propane; 1,1-bis(4-hydroxyphenyl)cyclohexane; 1,1-bis(4-hydroxy-3-methylphenyl)cyclohexane and 1,1-bis(4-hydroxyphenyl)-3,3,5-trimethylcyclohexane, may be prepared by the method of the present invention. The present invention is best exemplified by its use in the preparation of bisphenol A via condensation reaction of the hydroxyaromatic compound, phenol, and the ketone, acetone. A mixture comprising phenol and acetone may be contacted with an amine modified acidic resin catalyst and thiol promoter at a temperature between about 20° C. and about 100° C., preferably between about 40° C. and about 90° C. and still more preferably between about 50° C. and about 80° C.

The method of the present invention may be employed in both batch and continuous processes. When the method of the present invention is employed as a continuous process, the amine modified acidic resin catalyst may be configured in a fixed bed or stirred tank reactor such that the reactants, phenol, acetone and the thiol promoter are presented to the catalyst and removed from the catalyst in a continuous fashion. Alternatively, the amine modified acidic resin catalyst may be pretreated with the thiol promoter containing a functional group such as an amine or a carbamate capable of attachment to the amine modified acidic resin catalyst. The use of an attached thiol promoter obviates the need to include thiol promoter in the feed stream comprising phenol and acetone. Where a thiol promoter containing a basic functional group is employed, it may be attached to the amine modified acidic resin itself or it may be included in the during the preparation of the amine modified acidic resin from an unmodified acidic resin.

When the method of the present invention is employed as a continuous process, the reactants are combined to give a feed mixture said mixture being introduced at a weight hourly space velocity of from about 0.1 to about 6, preferably from about 1 to about 4, and even more preferably from about 2 to about 3.5 pounds of the feed mixture per pound catalyst per hour. The feed mixture comprises from about 0.1 to about 10 weight percent acetone and about 70 to about 99 weight percent phenol, preferably about 3 to about 8 weight percent acetone and about 85 to about 96 weight percent phenol, and still more preferably about 3 to about 6 weight percent acetone and about 90 to about 96 weight percent phenol. When employed as a bulk promoter, the thiol promoter may be present in an amount in a range between about 5 and about 100, preferably about 10 and about 75, and even more preferably about 20 and about 40 millimoles per liter (mmol/L) of feed. When employed as an attached promoter the thiol is present in an amount in a range between about 0.1 and about 3, preferably about 0.5 and about 2 milliequivalents per gram amine modified acidic resin catalyst.

EXAMPLES

The following examples are put forth so as to provide those of ordinary skill in the art with a detailed disclosure and description of how the methods claimed herein are evaluated. Unless indicated otherwise, parts are by weight, temperature is in degrees centigrade. The materials and testing procedures used for the results shown herein are as follows:

Starting material and product compositions were determined by gas chromatography on a Hewlett Packard model 5890 gas chromatograph. GC-mass spectral data were obtained on a Hewlett Packard model 5971A GC-MS. The laboratory robot employed was an 8-probe Gilson 215 modified to be able to transfer molten phenolic solutions. The reaction block was heated by means of a heating block and the reaction temperature was 70° C. +/–1° C.

The surprising effect of amine modified acidic resin catalysts was demonstrated on a laboratory scale in a reaction vessel designed to act as a stirred tank reactor operated in a continuous mode. Sampling was carried out under steady state conditions. Modification of the acidic resin catalysts was carried out as follows. Each well of a septum-sealed 96 well polypropylene block, equipped with miniature magnetic bars, was charged with a solid acidic resin catalyst (47–49 milligrams), such as Amberlyst® 131, and, by means of a laboratory robot, a solution containing an amine, such as pyridine, and optionally containing a thiol promoter capable of attachment to the resin, such as cysteamine. The amount of amine and promoter was such that from 5 to 50 percent of the total number of acid sites on the resin were neutralized. Where the thiol promoter did not contain a basic functional group, such as an amine, whereby it could be attached to the acidic resin catalyst, it was not included with the amine during the catalyst modification step and was instead added as part of the phenol-acetone feed mixture. The mixture of the solid acidic resin catalyst and phenol containing amine and optionally the thiol promoter was stirred and heated at 70° C. for a period of about 1 hour to afford the amine modified acidic resin catalyst. Reactants phenol, acetone and optionally the thiol promoter were then added and the mixture was then stirred and heated for at period of seven minutes at 70° C. at which point a portion of the reaction mixture was removed, care being taken to assure that the supernatant liquid and not the solid catalyst are removed. After an additional period of seven minutes, reactant solution was added in an amount equal to the volume removed in the previous step. This "making up" of the reaction volume with fresh reactants completes a cycle. Liquid residence time was about 1 hour and the thoughput of stock solution was about 3 grams of stock solution per gram resin catalyst per hour. After 40 cycles the reaction mixture was considered to have achieved a steady state and the reaction mixture was sampled and analyzed by gas chromatography. Each reaction was run in duplicate.

Examples 1–35 and Comparative Examples 1–6

The reactors were charged with 4% crosslinked sulfonated polystyrene beads and treated with the amines indicated in Table 1 as described in the general experimental section. The stock solution of reactants contained about 4.5 weight percent acetone, about 95 weight percent phenol. The stock solution further comprised the thiol promoter (3-mercaptopropionic acid, benzyl mercaptan, or trimethulsilylmethanethiol) at a concentration in a range between about 20.5 and about 41 millimoles per liter. Data are provided in Tables 1–3. Examples 1–35 demonstrate the improved selectivity of the amine modified acidic resin catalyst. Comparative Examples 1–6 illustrate the lower selectivity attendant upon the use of unmodified acidic resin catalyst.

TABLE 1

THIOL PROMOTER IS 3-MERCAPTOPROPIONIC ACID

| Example | thiol promoter mmol/L[b] | amine[c] | amine loading Meq/gram[d] | pp/op avg[e] | pp-BPA sel avg[f] |
|---|---|---|---|---|---|
| 1 | 20.5 | pyridine | 0.5 | 15.42 | 92.64 |
| 2 | 20.5 | pyridine | 1 | 16.77 | 93.20 |
| 3 | 20.5 | pyridine | 1.5 | 18.37 | 93.79 |
| 4 | 20.5 | triethylamine | 0.5 | 15.35 | 92.45 |
| 5 | 20.5 | triethylamine | 1 | 16.70 | 93.18 |
| 6 | 20.5 | triethylamine | 1.5 | 18.56 | 93.80 |
| CE-1[a] | 20.5 | | 0 | 14.35 | 91.98 |
| 7 | 41 | pyridine | 0.5 | 17.69 | 93.36 |
| 8 | 41 | pyridine | 1 | 19.58 | 94.01 |
| 9 | 41 | pyridine | 1.5 | 22.05 | 94.67 |
| 10 | 41 | triethylamine | 0.5 | 17.33 | 93.33 |
| 11 | 41 | triethylamine | 1 | 20.09 | 94.13 |
| 12 | 41 | triethylamine | 1.5 | 23.06 | 94.68 |
| CE-2[a] | 41 | | 0 | 15.95 | 92.70 |

[a]Comparative Example
[b]Concentration of in millimoles per liter
[c]Amine used to modify acidic resin catalyst
[d]Milliequivalents amine per gram acidic resin catalyst
[e]Selectivity expressed as weight percent p,p-BPA present in the reaction mixture divided by the weight percent o,p-BPA present in the reaction mixture
[f]Selectivity expressed as weight % p,p-BPA in product mixture relative to all other phenol/acetone condensation products present in the reaction mixture.

TABLE 2

THIOL PROMOTER IS BENZYL MERCAPTAN

| Example | thiol promoter mmol/L[b] | amine[c] | amine loading Meq/gram[d] | pp/op avg[e] | pp-BPA sel avg[f] |
|---|---|---|---|---|---|
| 13 | 20.5 | pyridine | 0.5 | 15.57 | 92.62 |
| 14 | 20.5 | pyridine | 1 | 17.70 | 93.48 |
| 15 | 20.5 | pyridine | 1.5 | 20.66 | 94.31 |
| 16 | 20.5 | triethylamine | 1 | 17.68 | 93.38 |
| 17 | 20.5 | triethylamine | 1.5 | 20.77 | 94.31 |
| CE-3[a] | 20.5 | | 0 | 14.38 | 91.97 |
| 18 | 41 | pyridine | 0.5 | 17.98 | 93.45 |
| 19 | 41 | pyridine | 1 | 20.79 | 94.23 |
| 20 | 41 | pyridine | 1.5 | 24.15 | 95.03 |
| 21 | 41 | triethylamine | 0.5 | 17.96 | 93.41 |
| 22 | 41 | triethylamine | 1 | 21.34 | 94.43 |
| 23 | 41 | triethylamine | 1.5 | 25.42 | 95.12 |
| CE-4[a] | 41 | | 0 | 15.59 | 92.42 |

[a]Comparative Example
[b]Concentration of in millimoles per liter
[c]Amine used to modify acidic resin catalyst
[d]Milliequivalents amine per gram acidic resin catalyst
[e]Selectivity expressed as weight percent p,p-BPA present in the reaction mixture divided by the weight percent o,p-BPA present in the reaction mixture
[f]Selectivity expressed as weight % p,p-BPA in product mixture relative to all other phenol/acetone condensation products present in the reaction mixture.

TABLE 3

THIOL PROMOTER IS TRIMETHYLSILYLMETHANETHIOL

| Example | thiol promoter mmol/L[b] | amine[c] | amine loading Meq/gram[d] | pp/op avg[e] | pp-BPA sel avg[f] |
|---|---|---|---|---|---|
| 24 | 20.5 | pyridine | 0.5 | 18.80 | 93.67 |
| 25 | 20.5 | pyridine | 1 | 21.60 | 94.49 |
| 26 | 20.5 | pyridine | 1.5 | 24.78 | 95.11 |
| 27 | 20.5 | triethylamine | 0.5 | 18.58 | 93.63 |
| 28 | 20.5 | triethylamine | 1 | 22.34 | 94.64 |
| 29 | 20.5 | triethylamine | 1.5 | 26.40 | 95.24 |
| CE-5[a] | 20.5 | | 0 | 16.38 | 92.80 |
| 30 | 41 | pyridine | 0.5 | 20.43 | 94.14 |
| 31 | 41 | pyridine | 1 | 24.10 | 94.95 |
| 32 | 41 | pyridine | 1.5 | 27.73 | 95.44 |
| 33 | 41 | triethylamine | 0.5 | 20.52 | 94.10 |
| 34 | 41 | triethylamine | 1 | 25.39 | 95.11 |
| 35 | 41 | triethylamine | 1.5 | 29.31 | 95.62 |
| CE-6[a] | 41 | | 0 | 17.44 | 93.19 |

[a]Comparative Example
[b]Concentration of in millimoles per liter
[c]Amine used to modify acidic resin catalyst
[d]Milliequivalents amine per gram acidic resin catalyst
[e]Selectivity expressed as weight percent p,p-BPA present in the reaction mixture divided by the weight percent o,p-BPA present in the reaction mixture
[f]Selectivity expressed as weight % p,p-BPA in product mixture relative to all other phenol/acetone condensation products present in the reaction mixture.

Examples 36–55 and Comparative Examples 7–10

The reactors were charged with 4% crosslinked sulfonated polystyrene beads and treated with the amine and thiol promoter cysteamine as described in the general experimental section. The total amount of amine and attached thiol promoter cysteamine was between about 0.5 and about 2 milliequivalents per gram resin catalyst. The stock solution of reactants contained about 4.5 weight percent acetone, about 95.5 weight percent phenol. Data are provided in Table 4. Examples 36–55 demonstrate excellent selectivities for amine modified acidic resin catalysts containing the attached promoter cysteamine. For example, Examples 36–40 and Comparative Example 7 illustrate that the selectivity observed at 2 milliequivalents cysteamine per gram acidic resin catalyst is maintained for amine modified acidic resin catalysts containing pyridine in which the total amine content is held constant. The data demonstrate that lower levels of cysteamine may be employed without sacrificing selectivity in the formation of bisphenol A. Examples 41–45 and Comparative Example 8 reveal the same effect in a different concentration regime as do Examples 46–50 and Comparative Example 9. Examples 51–55 and comparative Example 10 illustrate that at relatively low levels of amine, 0.5 milliequivalents per gram acidic resin catalyst, the system affords lower selectivity for p,p-BPA formation as cysteamine is replaced by pyridine.

TABLE 4

ATTACHED PROMOTER ON AMINE MODIFIED ACIDIC RESIN CATALYST

| Example | Total b amine meq/g | Pyridine c meq/g | Cysteamine d meq/gram | BPA selectivity e avg |
|---|---|---|---|---|
| CE-7[a] | 2 | 0 | 2 | 94.95 |
| 36 | 2 | 0.4 | 1.6 | 95.01 |
| 37 | 2 | 0.8 | 1.2 | 95.19 |
| 38 | 2 | 1.2 | 0.8 | 95.40 |
| 39 | 2 | 1.6 | 0.4 | 95.17 |
| 40 | 2 | 1.8 | 0.2 | 95.14 |
| CE-8 | 1.5 | 0 | 1.5 | 94.89 |
| 41 | 1.5 | 0.3 | 1.2 | 94.87 |
| 42 | 1.5 | 0.6 | 0.9 | 94.85 |
| 43 | 1.5 | 0.9 | 0.6 | 94.97 |

TABLE 4-continued

ATTACHED PROMOTER ON AMINE MODIFIED ACIDIC RESIN CATALYST

| Example | Total b amine meq/g | Pyridine c meq/g | Cysteamine d meq/gram | BPA selectivity e avg |
|---|---|---|---|---|
| 44 | 1.5 | 1.2 | 0.3 | 94.72 |
| 45 | 1.5 | 1.35 | 0.15 | 94.36 |
| CE-9 | 1 | 0 | 1 | 94.29 |
| 46 | 1 | 0.2 | 0.8 | 94.27 |
| 47 | 1 | 0.4 | 0.6 | 94.25 |
| 48 | 1 | 0.6 | 0.4 | 94.15 |
| 49 | 1 | 0.8 | 0.2 | 93.74 |
| 50 | 1 | 0.9 | 0.1 | 93.43 |
| CE-10[a] | 0.5 | 0 | 0.5 | 93.60 |
| 51 | 0.5 | 0.1 | 0.4 | 93.48 |
| 52 | 0.5 | 0.2 | 0.3 | 93.24 |
| 53 | 0.5 | 0.3 | 0.2 | 93.05 |
| 54 | 0.5 | 0.4 | 0.1 | 92.25 |
| 55 | 0.5 | 0.45 | 0.05 | 91.75 |

[a]Comparative Example
b Total amount of cysteamine and pyridine expressed as milliequivalents per gram acidic resin
c Milliequivalents pyridine per gram acidic resin catalyst
d Milliequivalents cysteamine per gram acidic resin catalyst
e Selectivity expressed as weight % p,p-BPA in product mixture relative to all other phenol/acetone condensation products present in the reaction mixture.

PREPARATION OF SILYLMETHANETHIOL DERIVATIVE VII

A 250 mL 3-necked round bottom flask equipped with reflux condenser nitrogen inlet, thermometer heating mantle, pressure equalizing addition funnel and magnetic stirrer was charged with 14.36 g (91.3 mmol) of t-butyl N-allylcarbamate and 150 mL of toluene. The olefin and solvent were stirred and heated to about 70° C., then 10 microliters of Karstedt's catalyst (5% Pt solution, about 30 ppm Pt based on olefin) was added. A solution containing 12 g (110.5 mmol) of chloromethyldimethylsilane in 20 mL toluene was added cautiously over about 30 minutes at a rate sufficient to maintain the reaction temperature between about 80 and about 100° C. After addition was completed, the temperature was stirred and heated at about 85° for about 1 hour. GC-MS indicated complete reaction of the olefin to form the silylated compound, N-Boc-3-aminopropylchloromethyldimethylsilane. The solution was transferred to a 500 ml single neck round bottom flask and the solvent and excess silane were stripped via rotary evaporation to yield 25 g of crude product (quantitative yield based on olefin).

Solid potassium thioacetate (1.37 g, 0.012 mol) was charged to a 125 mL reaction bottle equipped with a magnetic stirrer in a nitrogen filled dry box. The bottle was fitted with a septum and removed from the dry box. Methanol (30 mL) was added and the mixture was stirred to dissolve the potassium thiol acetate. Crude N-Boc-3-aminopropylchloromethyldimethylsilane (2.65 g, 0.01 mol) was then added via syringe and the mixture was warmed to about 50° for about 4.5 hr. Thereafter the mixture was allowed to stand at room temperature for about 48 hr. Water (50 mL) and methylene chloride (50 mL) were added and the phases separated. The organic layer was washed twice with water, dried over sodium sulfate, filtered through a column of silica gel and concentrated under reduced pressure to afford the N-Boc-3-aminopropyldimethylsilylmethanethiol acetate derivative VII (2.84 g) as a nearly colorless oil the $^1$H-NMR, $^{13}$C-NMR and GC-MS of which were fully consistent with structure VII.

The invention has been described in detail with particular reference to preferred embodiments thereof, but it will be understood that variations and modifications can be effected within the spirit and scope of the invention.

What is claimed is:

1. A method for making a bisphenol, said method comprising contacting a mixture comprising a hydroxyaromatic compound and a ketone or an aldehyde with an amine modified acidic resin catalyst at a temperature in a range between about 25° C. and about 95° C. in the presence of a thiol promoter, said amine modified acidic resin catalyst being prepared from an acidic resin comprising acidic functional groups by neutralizing a portion of said acidic functional groups with an amine, said amine being distinct from any thiol promoter which itself comprises an amine group.

2. A method according to claim 1 wherein said amine modified acidic resin catalyst is prepared from a sulfonated polystyrene having repeat units I.

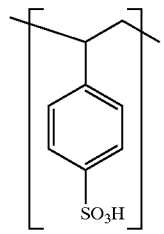

I

3. A method according to claim 2 wherein said amine modified acidic resin catalyst comprises from about 0.1 to about 6 milliequivalents of sulfonic acid groups per gram of resin.

4. A method according to claim 1 wherein the amine employed in the preparation of the amine modified acidic resin is an aliphatic amine, an aromatic amine or a cycloaliphatic amine.

5. A method according to claim 4 wherein said amine modified acidic resin catalyst comprises from about 0.005 to about 3 milliequivalents of amine per gram of resin.

6. A method according to claim 5 wherein said amine is selected from the group consisting of triethylamine, trimethylamine, tributylamine, N,N-dimethylbutyamine, piperidine, morpholine, 1,8-diazabicyclo[5.4.0]undec-7ene (DBU), diazabicylco[2.2.2]octane, pyridine, imidazole, quinoline and piperazine.

7. A method according to claim 1 wherein said thiol promoter is selected from the group consisting of aliphatic thiols, cycloaliphatic thiols and aromatic thiols.

8. A method according to claim 7 wherein said aliphatic thiol is a silylmethanethiol having structure II

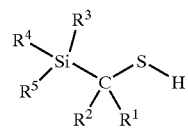

II wherein $R^1$ and $R^2$ are each independently hydrogen, a $C_1$–$C_{40}$ aliphatic radical, a $C_3$–$C_{40}$ aromatic radical, a $C_3$–$C_{40}$ cycloaliphatic radical, or
  $R^1$ and $R^2$ together form a $C_3$–$C_{40}$ cycloaliphatic radical or a $C_4$–$C_{40}$ aromatic radical;
  $R^3$–$R^5$ are each independently a $C_1$–$C_{40}$ aliphatic radical, a $C_3$–$C_{40}$ aromatic radical, or a $C_3$–$C_{40}$ cycloaliphatic radical; or any two of the groups R³–R⁵ together form a C₅–C₄₀ cycloaliphatic radical or C₅–C₄₀ aromatic radical; or the groups R³–R⁵ together form a C₉–C₄₀ cycloaliphatic radical or C₁₀–C₄₀ aromatic radical.

9. A method according to claim 8 wherein said silylmethanethiol promoter is selected from the group consisting of trimethylsilylmethanethiol, triethylsilylmethanethiol, tripropylsilylmethanethiol, tributylsilylmethanethiol, 1-trimethylsilyl-1-ethylmethanethiol and 1-trimethylsilyl-1-benzylmethanethiol.

10. A method according to claim 8 wherein said silylmethanethiol is selected from the group consisting of 3-N-methylaminopropyldimethylsilylmethanethiol, 3-N,N-dimethylaminopropyldimethylsilylmethanethiol and 3-(1-piperadinyl)propyldimethylsilylmethanethiol.

11. A method according to claim 7 wherein said thiol promoter is not adapted for attachment to an acidic resin.

12. A method according to claim 11 wherein said thiol promoter is selected from the group consisting of benzylthiol, butanethiol, hexanethiol, octadecanethiol and 3-mercaptopropionic acid.

13. A method according to claim 11 wherein said thiol promoter is present in an amount in the range of from about 5 mmol/L and about 100 mmol/L of feed.

14. A method according to claim 7 wherein said thiol promoter comprises a functional group selected from the group consisting of amine groups, amido groups, imido groups, and carbamyl groups.

15. A method according to claim 14 wherein said thiol promoter is selected from the group consisting of 2-mercaptomethylpyridine, cysteamine, and 4-aminobutanethiol.

16. A method according to claim 14 wherein said thiol promoter is present in an amount in a range between about 0.1 and about 3 milliequivalents per gram amine modified acidic resin catalyst.

17. A method according to claim 1 wherein the bisphenol is selected from the group consisting of 2,2-bis(4-hydroxyphenyl)propane; 2,2-bis(4-hydroxy-3-methylphenyl)propane; 1,1-bis(4-hydroxyphenyl)cyclohexane; 1,1-bis(4-hydroxy-3-methylphenyl)cyclohexane, 1,1-bis(4-hydroxyphenyl)-3,3,5-trimethylcyclohexane and 9,9-Bis(4-hydroxyphenyl)fluorene.

18. A method according to claim 1 wherein said mixture comprising a hydroxyaromatic compound and a ketone or an aldehyde contains from about 0.1 to about 10 weight percent acetone and from about 70 to about 99 weight percent phenol.

19. A method for making bisphenol A, said method comprising contacting a mixture of phenol and acetone and a thiol promoter in the presence of an amine modified acidic resin catalyst at a temperature in a range between about 50° C. and about 80° C., said phenol being present in an amount in a range between about 90 and about 95 percent by weight, said acetone being present in an amount in a range between about 4 and about 6 percent by weight, said thiol promoter being present in an amount between about 10 and about 100 mmol/L of reactants, said amine modified acidic resin catalyst being prepared from an acidic resin comprising acidic functional groups by neutralizing a portion of said acidic functional groups with an amine, said amine being distinct from any thiol promoter which itself comprises an amine group.

20. A method according to claim 19 wherein the amine modified acidic resin catalyst comprises from about 2 to about 4.5 milliequivalents of sulfonic acid groups per gram and from about 0.5 to about 3 milliequivalents of amine per gram.

21. A method according to claim 20 wherein the amine is selected from the group consisting of triethylamine and pyridine.

22. A method for making bisphenol A, said method comprising contacting a mixture of phenol and acetone in the presence of an amine modified acidic resin catalyst at a temperature in a range between about 50° C. and about 80° C., said phenol being present in an amount in a range between about 90 and about 95 percent by weight of said mixture, said acetone being present in an amount in a range between about 4 and about 6 percent by weight of said mixture, said amine modified acidic resin catalyst being prepared from an acidic resin comprising acidic functional groups by neutralizing a portion of said acidic functional groups with an amine, said amine being distinct from any thiol promoter which itself comprises an amine group, said amine modified acidic resin catalyst further comprising a thiol promoter, said thiol promoter containing a functional group selected from the group consisting of amino groups, amido groups, imido groups and carbamyl groups; said thiol promoter being present in an amount between about 0.5 and about 2 mmol per gram of resin.

23. A method according to claim 22 wherein said thiol promoter is selected from the group consisting of cysteamine and 3-aminopropyldimethylsilylmethanethiol.

24. An amine modified acidic resin catalyst, said amine modified acidic resin catalyst being prepared from an acidic resin comprising acidic functional groups by neutralizing a portion of said acidic functional groups with an amine, said amine being distinct from any thiol promoter which itself comprises an amine group, said catalyst comprising: sulfonated polystyrene units I

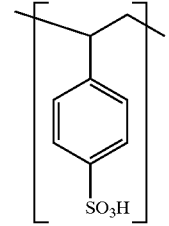

I and residues derived from the group consisting of aromatic amines, aliphatic amines and cycloaliphatic amines; said catalyst further comprising a thiol promoter comprising an amino, amido, imido, or carbamyl group.

25. An amine modified acidic resin catalyst according to claim 24 wherein the amine is selected from the group consisting of pyridine and triethylamine.

26. An amine modified acidic resin catalyst according to claim 24 wherein the thiol promoter is selected from the group consisting of 3-aminopropyldimethylsilylmethanethiol, 3-N-methylaminopropyldimethylsilylmethanethiol, 3-N,N-dimethylaminopropyldimethylsilylmethanethiol, 3-(1-piperadinyl)propyldimethylsilylmethanethiol and 2-(4-pyridyl)ethyldimethylsilylmethanethiol.

27. An amine modified acidic resin catalyst according to claim 24 wherein the thiol promoter is selected from the group consisting of cysteamine and 2-mercaptomethylpyridine.

* * * * *